United States Patent
Ryan (10) Patent No.: US 11,684,382 B2
(45) Date of Patent: Jun. 27, 2023

(54) WOUND VISUALIZATION FORCEPS AND METHOD

(71) Applicant: Edwin Ryan, St. Paul, MN (US)

(72) Inventor: Edwin Ryan, St. Paul, MN (US)

(73) Assignee: Edwin Ryan, St. Paul, MN (US)

( * ) Notice: Subject to any disclaimer, the term of this patent is extended or adjusted under 35 U.S.C. 154(b) by 126 days.

(21) Appl. No.: 17/401,077

(22) Filed: Aug. 12, 2021

(65) Prior Publication Data

US 2022/0047289 A1 Feb. 17, 2022

Related U.S. Application Data (60) Provisional application No. 63/066,175, filed on Aug. 15, 2020.

(51) Int. Cl.
| | |
|---|---|
| *A61B 17/30* | (2006.01) |
| *A61B 17/04* | (2006.01) |
| *A61B 17/02* | (2006.01) |
| *A61F 9/007* | (2006.01) |
| *A61B 17/00* | (2006.01) |

(52) U.S. Cl.
CPC .......... *A61B 17/30* (2013.01); *A61B 17/0231* (2013.01); *A61B 17/0483* (2013.01); *A61F 9/007* (2013.01); *A61B 2017/00902* (2013.01)

(58) Field of Classification Search
CPC . A61B 17/30; A61B 17/0231; A61B 17/0483; A61B 2017/00902; A61B 17/0482; A61B 2017/00907; A61F 9/007; B25B 9/02; A45D 26/0066; A47G 21/10
See application file for complete search history.

(56) References Cited

U.S. PATENT DOCUMENTS

| | | | | |
|---|---|---|---|---|
| 2004/0006357 | A1* | 1/2004 | Baldesberger | B25B 9/02 606/167 |
| 2004/0153121 | A1* | 8/2004 | Pietrabissa | A61B 17/2841 606/205 |
| 2008/0243181 | A1* | 10/2008 | Schneider | B25B 9/02 362/572 |
| 2009/0138029 | A1* | 5/2009 | Saliman | A61B 17/0469 606/139 |
| 2010/0130990 | A1* | 5/2010 | Saliman | A61B 17/0469 606/145 |
| 2011/0218557 | A1* | 9/2011 | Saliman | A61B 17/04 606/145 |
| 2011/0270280 | A1* | 11/2011 | Saliman | A61B 17/0469 606/145 |

\* cited by examiner

*Primary Examiner* — George J Ulsh
(74) *Attorney, Agent, or Firm* — Schwegman Lundberg & Woessner, P.A.

(57) ABSTRACT

Devices and methods to stabilize an eye and suture with wound visibility are shown. In selected examples, a forceps is shown that includes one or more transparent projections. In use, the one or more transparent projections can be concurrently pressed against the wound while holding an eye stable with gripping surfaces of the forceps. The one or more transparent projections and the gipping of the forceps work together to aid in a suture placement.

18 Claims, 5 Drawing Sheets

WOUND VISUALIZATION FORCEPS AND METHOD

CLAIM OF PRIORITY

This application claims the benefit of priority under 35 U.S.C. § 119(e) to U.S. Patent Application Ser. No. 63/066,175, filed on Aug. 15, 2020, which is incorporated by reference herein in its entirety.

BACKGROUND

A number of ophthalmological procedures require access to the inner eye. In these procedures, a wound in the eye is necessary to pass instruments though and perform the procedure on tissues inside the eye. The wounds can be difficult to see, due to fluids present around the wound, and due to the natural tendency of the tissues about the wound to press closed, which may obscure the location of the wound. Additionally, it can be difficult to suture a wound due to the resistance of the tissues to insertion of a needle.

Improved devices for suturing wounds in an eye and methods are desired that address these and other problems.

DETAILED DESCRIPTION

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

Figure 1:
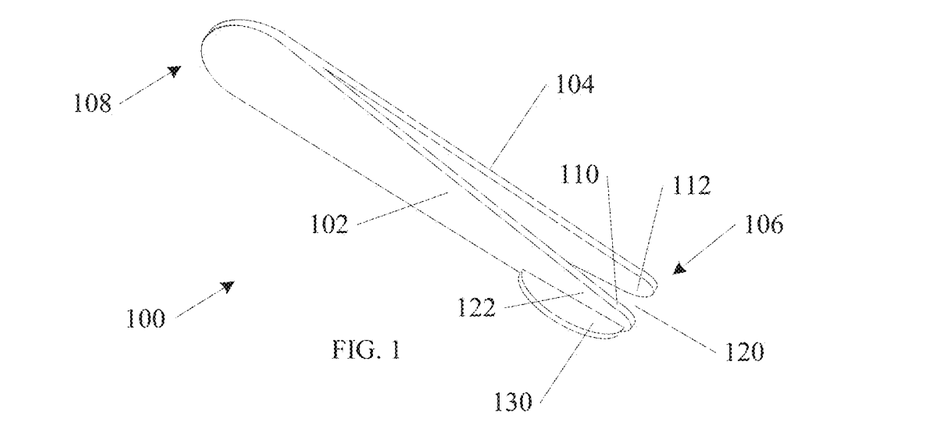
FIG. 1 shows a forceps according to an embodiment of the invention.

FIG. 1 shows a forceps 100 according to one example. The forceps 100 includes a first arm 102 and a second arm 104. The forceps further includes a distal end 106 and a proximal end 108. The first arm 102 has a first gripping surface 110 located at the distal end 106 of the first arm 102. Similarly, the second arm 104 has a second gripping surface 112 located at the distal end 106 of the second arm 104.

A gripping region 120 is shown between the first gripping surface 110 and the second gripping surface 112. A first lateral region 122 is shown located on a side of the first arm 102 opposite the gripping region 120.

Figure 2:
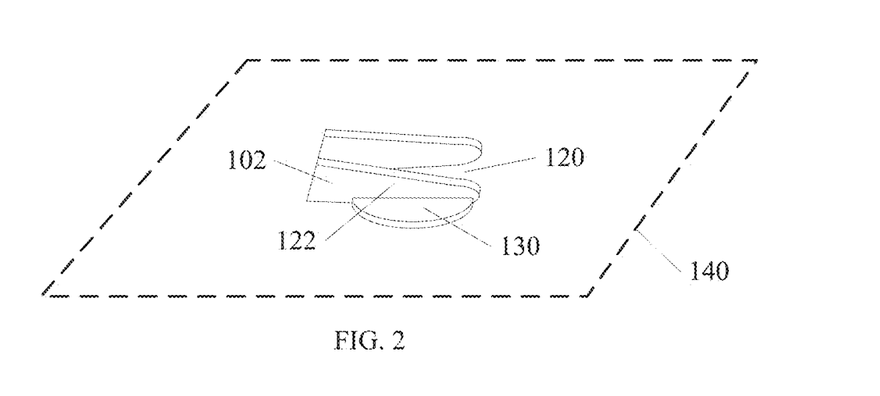
FIG. 2 shows a distal portion of the forceps from FIG. 1 according to an embodiment of the invention.

FIG. 2 shows a view of only a portion of the forceps 100 at the distal end 106. The end of the forceps defines a bottom plane 140 as shown in FIG. 2. A transparent projection 130 is shown extending from the lateral region 122. Although the term transparent is used to describe the transparent projection 130, it will be appreciated that different levels of transparency are within the scope of the invention. A translucent projection is within the scope of the invention, provided that a wound is sufficiently visible through the projection material as described in more detail below. In one example, as illustrated in FIGS. 2 and 3, a bottom surface of the transparent projection 130 is within the bottom plane 140 of the forceps.

In one example, the transparent projection is formed from a polymeric material, such as polycarbonate, or other transparent polymer. In one example, the transparent projection is formed from glass. In one example, one or more arms of the forceps are formed from a metal. In one example, the metal is stainless steel. Metal forceps and a glass transparent projection may better facilitate sterilization and re-use.

In one example, one or more arms of the forceps are formed from a polymeric material. In one example, the transparent projection is formed from a polymeric material that is different from the polymeric material of the one or more arms of the forceps. In one example, the different polymeric materials of the arms and the transparent projection are co-molded to form an integral forceps with a transparent projection. Co-molding may provide a simple and inexpensive way to manufacture a forceps with different properties such as transparency and spring like resiliency for arms, wherein a single manufacturing process is used. In one example, a polymeric forceps is inexpensive enough to be disposable and need not be capable of sterilization. In one example, a polymeric disposable forceps may be included in a surgery kit, along with other tools, for an intended procedure where the forceps are used as described in the present disclosure to close a wound after the procedure is complete.

Figure 3:
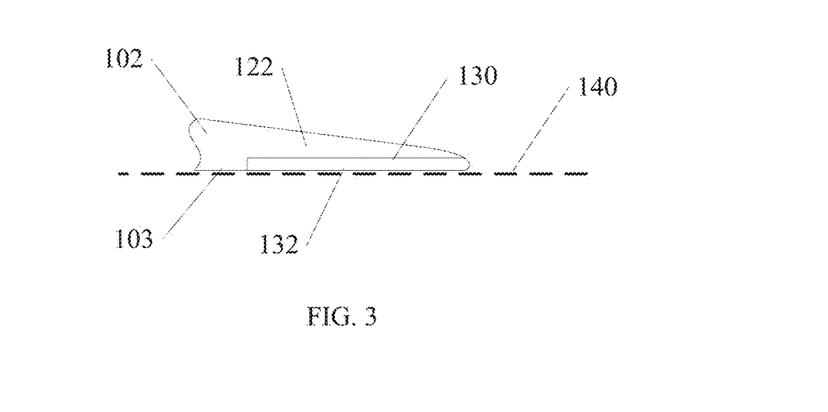
FIG. 3 shows a side view of a distal portion of the forceps from FIG. 1 according to an embodiment of the invention.

FIG. 3 shows a side view of the distal end 106 of the forceps 100. The bottom plane 140 is shown in FIG. 3 and FIG. 2. As shown in FIG. 3, a bottom surface 132 of the transparent projection 130 is within the bottom plane 140 of the forceps 100. In one example, as described in more detail below, the bottom surface 132 of the transparent projection 130 is pressed against a wound to push any fluids out of the way and in some examples, to open the wound slightly. The removal of fluids and/or the opening of the wound provides better visibility of the wound to a surgeon. This facilitates easier placement of one or more sutures to close the wound. In one example, the forceps 100 are used to both grasp a portion of the eye and to concurrently enhance visibility of the wound as described above. The location of the bottom surface 132 within the bottom plane 140 of the forceps 100 makes the forceps more effective at both grasping and pressing the bottom surface 132 against a wound at the same time.

Although location of the bottom surface 132 within the bottom plane 140 is shown, the invention is not so limited. For example, the transparent projection may be located on an end surface instead of a bottom surface, and still function as intended to provide concurrent gripping of an eye, and pressure of the transparent projection against a wound.

Further, although a flat surface of the transparent projection 130 is described, the invention is not so limited. Other examples include a curved bottom surface, or a textured bottom surface. Texturing a bottom surface of the transparent projection 130 may facilitate enhanced gripping of the eye.

Figure 4:
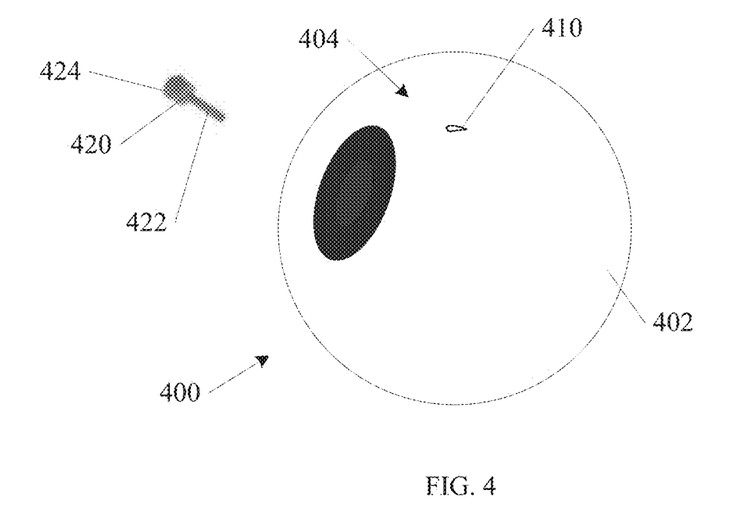
FIG. 4 shows an eye for performing a procedure according to an embodiment of the invention.

FIG. 4 shows a first stage 400 of an ophthalmic procedure according to one example. An eye 402 is shown with a wound 410 in a region 404 of the eye. In one example, the region 404 includes the conjunctiva of the eye 402. A trocar cannula 420 is shown adjacent to the eye 402. In one example, the wound 410 is a result of removal of the trocar cannula 402 after a procedure. In the example shown, the trocar cannula 420 includes a cannula 422 and a hub 424. The hub 424 is configured to stay outside the eye 402, while the cannula 422 enters the wound 410 and provides access to the interior of the eye 402 for any of a number of different types of intraocular procedures. Although a wound 410 from a procedure using a trocar cannula is illustrated as an example, the invention is not so limited. Forceps and methods described in the present disclosure can be used to suture other types of wounds and may be used with other procedures.

Figure 5:
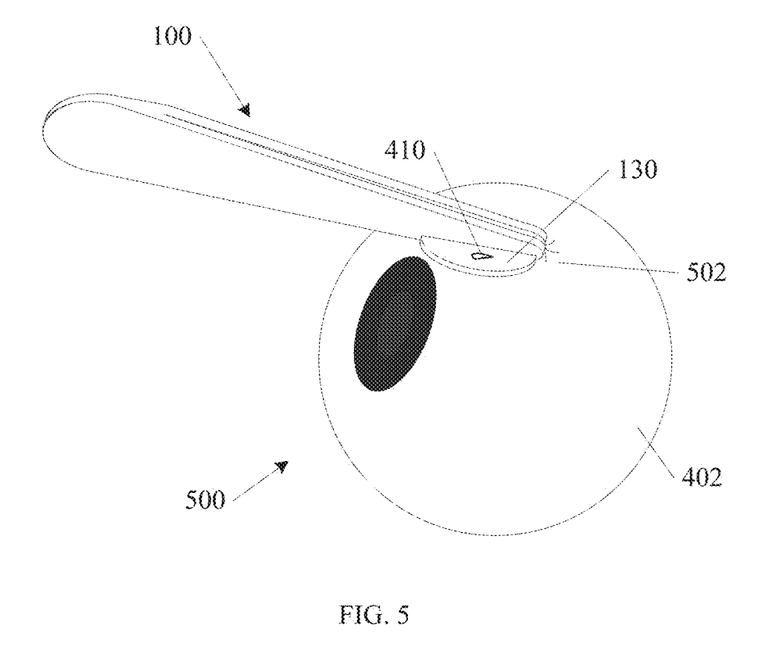
FIG. 5 shows the eye from FIG. 4 and a forceps performing part of a procedure according to an embodiment of the invention.

In the example shown in FIG. 4, the cannula 420 has been removed after completion of the procedure, and the wound 410 remains, and may require suturing to fully close the wound 410. In the stage illustrated in FIG. 5, the forceps 100 are shown gripping a portion 502 of the eye 402. In one example the forceps 100 are used to grip a portion 502 of the conjunctiva. As shown in FIG. 5, the portion 502 is adjacent to the wound 410. Because of the location of the portion 502 being adjacent to the wound, the transparent projection 130 is positioned to be pressed against the wound 410 concurrently with the gripping of the portion 502 of the eye 402.

In practice, fluids such as blood may be present around a wound, that obscure visualization of the wound. When the wound is obscured, it may be difficult to see an appropriate location for placement of a suture to help close the wound 410. By pressing the transparent projection 130 against the wound 410, fluids that may be present on the surface of the eye 401 around the wound 410 are driven away from an area adjacent to the wound 410. Because the transparent projection 130 is transparent, a surgeon can see the wound 410 more clearly through the transparent projection 130. Additionally, pressing the transparent projection 130 against the wound 410 may displace tissue around the wound, making it easier to see. For example, a closed slit may be difficult to see, while a slightly puckered slit resulting from light pressure of the transparent projection 130 may be easier to see.

In this way, pressing a transparent projection 130 against the wound 410 enhances visibility, and facilitates accurate placement of a suture. Because the transparent projection 130 is located at a distal end 106 of the forceps 100, it can be used with one hand during a procedure. The one hand of the surgeon can both grip a tissue of the eye 402 using the forceps, and position the transparent projection 130 against the wound 410 as shown in FIG. 5.

Figure 6:
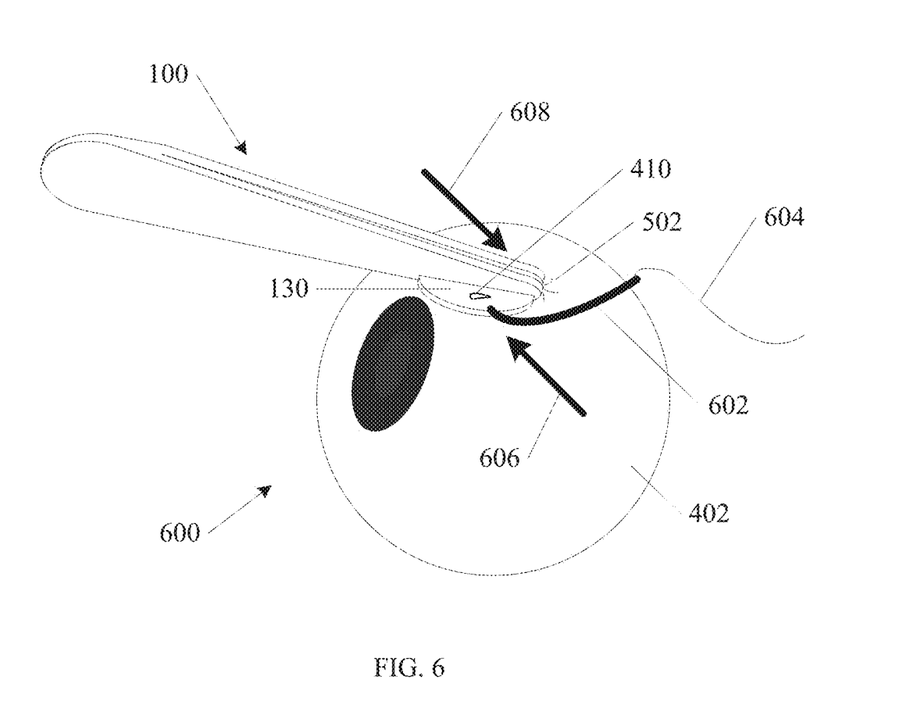
FIG. 6 shows the eye from FIG. 4 and a forceps performing another part of a procedure according to an embodiment of the invention.

FIG. 6 illustrates yet another stage in the procedure. A needle 602 is shown with a suture thread 604. Similar to FIG. 5, the wound 410 is visible through the transparent projection 130. As discussed above, the transparent projection 130 is pressed against the wound 410 to drive away fluids and otherwise enhance visibility of the wound 410. Concurrently with pressing the transparent projection 130 against the wound 410, the portion 502 of the eye 402 is gripped. In one example, the act of gripping the eye 402 further enhances stability of the eye during insertion of the needle 602. As shown in FIG. 6, insertion of the needle 602 involves force along direction 606. By gripping the eye 402 during insertion of the needle 602, a countering force 608 may be applied to stabilize the eye during insertion of the needle 602 and following suture 604.

Figure 7:
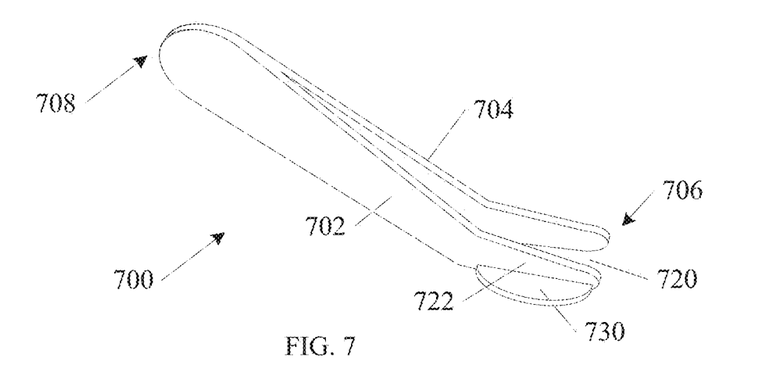
FIG. 7 shows a forceps according to an embodiment of the invention.

The preceding figures show one example configuration of a forceps 100 and a transparent projection 130 for illustrating the operating principles. The invention is not so limited to specific geometries, materials, etc. shown in the examples to this point. Fore example, FIG. 7 shows another forceps 700 according to one embodiment. The forceps 700 includes a first arm 702 and a second arm 704. The forceps further includes a distal end 706 and a proximal end 708. The first arm 702 has a first gripping surface 710 located at the distal end 706 of the first arm 702. Similarly, the second arm 704 has a second gripping surface 712 located at the distal end 706 of the second arm 704. A gripping region 720 is shown between the first gripping surface 710 and the second gripping surface 712. A first lateral region 722 is shown located on a side of the first arm 702 opposite the gripping region 720. A transparent projection 730 is shown extending from the lateral region 722.

In the example of FIG. 7, the distal end 706 of the forceps 700 is angled with respect to the proximal end 708 of the forceps. The angle may better facilitate a surgeon gripping an eye and concurrently pressing a transparent projection against a wound at the same time. Although a forceps that is hand held is shown, other examples are within the scope of the invention where a forceps are incorporated into a distal end of another instrument such as an illumination source, etc. Although typically arms of a forceps are connected at a proximal end as shown in the examples, the invention is not so limited. Functionally, as long as two arms meet at a distal end in a gripping surface, the addition of a transparent projection will provide the benefits described.

Figure 8:
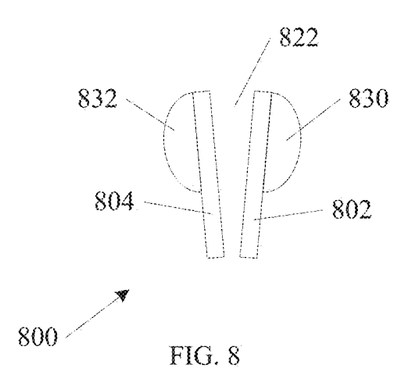
FIG. 8 shows a distal portion of a forceps according to an embodiment of the invention.

FIG. 8 shows another example of a distal end 800 of a forceps according to one example. A first arm 802 and a second arm 804 are shown. A gripping region 822 is shown between a first gripping surface and a second gripping surface of the arms 802, 804. A first transparent projection 830 is shown extending from a lateral region of the first arm 802. A second transparent projection 832 is further shown extending from a lateral region of the second arm 804. In one example, having two transparent projections 830, 832 on either side of the arms 802, 804 provides additional options for convenience in gripping a portion of an eye while concurrently pressing one of the two transparent projections 830, 832 against a wound. In one example, the options of two transparent projections 830, 832 may better facilitate a surgeon who is left or right-handed. The configuration may also provide a convenient option for a wound that is located in different portions of the eye.

Figure 9:
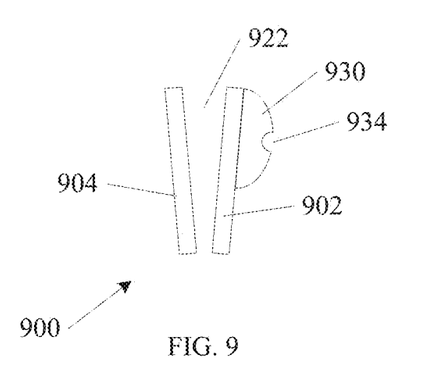
FIG. 9 shows a distal portion of a forceps according to an embodiment of the invention.

FIG. 9 shows another example of a distal end 900 of a forceps according to one example. A first arm 902 and a second arm 904 are shown. A gripping region 922 is shown between a first gripping surface and a second gripping surface of the arms 902, 904. A first transparent projection 930 is shown extending from a lateral region of the first arm 902. The example of FIG. 9 further includes one or more notches 934. In one example, a notch or notches may provide easy access for a needle to insert a suture while still providing a high degree of pressure to remove fluids and improve visualization of a wound. Although only one notch is shown, the invention is not so limited. In other examples multiple notches may provide options for a needle to enter and exit from an edge of a wound.

Although a semicircle or oval shape of a transparent projection is illustrated as an example, the invention is not so limited. Other shapes such as rectangular, curved, etc. are within the scope of the invention.

Features have been shown, including multiple transparent projections, notches, angled forceps, etc. One of ordinary skill in the art, having the benefit of the present disclosure, will recognize that combinations of these features and others, in any permutation, are within the scope of the invention.

Figure 10:
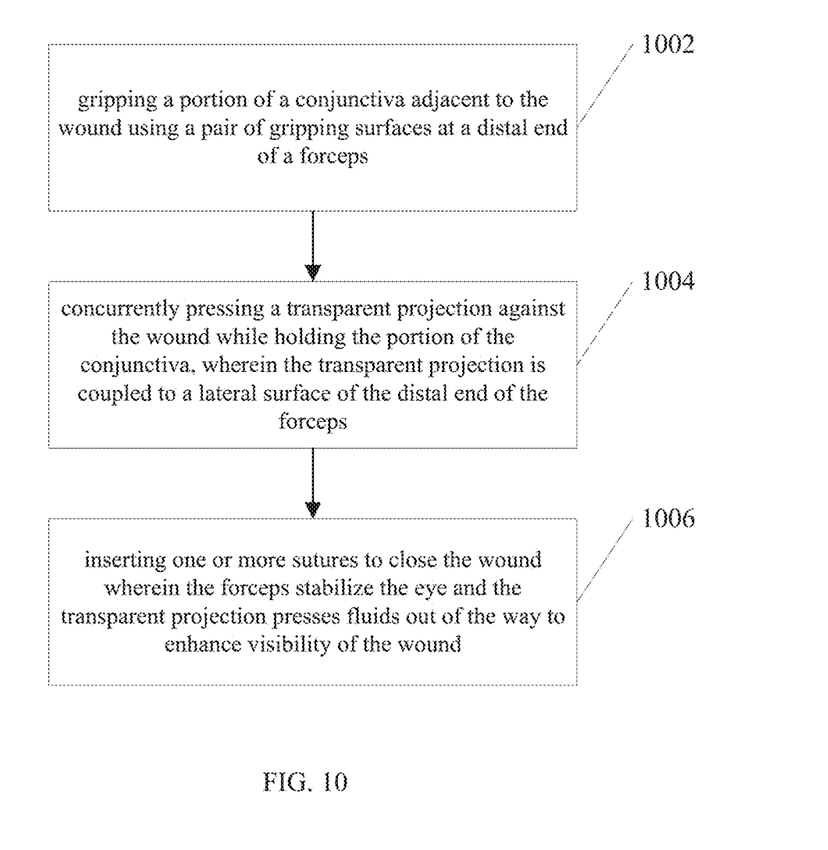
FIG. 10 shows a flow diagram of a method according to an embodiment of the invention.

FIG. 10 shows a flow diagram of a method of using a forceps according to one example. In operation 1002, a portion of a conjunctiva is gripped adjacent to the wound using a pair of gripping surfaces at a distal end of a forceps. In operation 1004, a transparent projection is concurrently pressed against the wound while holding the portion of the conjunctiva. In operation 1006, one or more sutures are inserted to close the wound wherein the forceps stabilize the eye and the transparent projection presses fluids out of the way to enhance visibility of the wound.

To better illustrate the method and apparatuses disclosed herein, a non-limiting list of embodiments is provided here:

Example 1 includes a forceps. The forceps includes a first arm, having a first gripping surface located at a distal end of the first arm, a second arm extending parallel to the first arm, having a second gripping surface located at a distal end of the second arm, and a gripping region between the first and second gripping surfaces. The forceps also includes a first lateral region on the first arm on a side opposite the gripping region, a bottom plane of the forceps defined by bottom edges of the first and second gripping surfaces, and a transparent projection extending from the first lateral region of the first arm, wherein a bottom surface of the transparent projection is within the bottom plane of the forceps.

Example 2 includes the forceps of example 1, wherein the first arm is connected to the second arm at a proximal end of the first and second arms.

Example 3 includes the forceps of any one of examples 1-2, wherein the transparent projection is formed from a polymeric material.

Example 4 includes the forceps of any one of examples 1-3, wherein the first and second arms are formed from stainless steel.

Example 5 includes the forceps of any one of examples 1-4, wherein the first and second arms are formed from a polymeric material, and the transparent projection is formed from a polymeric material.

Example 6 includes the forceps of any one of examples 1-5, wherein the first and second arms are co-molded with the transparent projection.

Example 7 includes the forceps of any one of examples 1-6, wherein the distal portion of the first and second arms is angled with respect to a proximal portion of the first and second arms.

Example 8 includes the forceps of any one of examples 1-7, wherein the transparent projection includes a cutout to allow closer insertion of a suture needle to a wound.

Example 9 includes a forceps. The forceps includes a first arm, having a first gripping surface located at a distal end of the first arm, a second arm extending parallel to the first arm, having a second gripping surface located at a distal end of the second arm, and a gripping region between the first and second gripping surfaces. The forceps also includes a first lateral region on the first arm on a side opposite the gripping region, a second lateral region on the second arm on a side opposite the gripping region, a bottom plane of the forceps defined by bottom edges of the first and second gripping surfaces. The forceps also includes a first transparent projection extending from the first lateral region of the first arm, wherein a bottom surface of the first transparent projection is within the bottom plane of the forceps, and a second transparent projection extending from the second lateral region of the second arm, wherein a bottom surface of the second transparent projection is within the bottom plane of the forceps.

Example 10 includes the forceps of example 9, wherein the distal portion of the first and second arms is angled with respect to a proximal portion of the first and second arms.

Example 11 includes the forceps of any one of examples 9-10, wherein the first and second transparent projections are formed from a polymeric material.

Example 12 includes the forceps of any one of examples 9-11, wherein the first and second arms are formed from stainless steel.

Example 13 includes the forceps of any one of examples 9-12, wherein the first and second arms are formed from a polymeric material, and the first and second transparent projections are formed from a polymeric material.

Example 14 includes the forceps of any one of examples 9-13, wherein the first and second arms are co-molded with the first and second transparent projections.

Example 15 includes a method of suturing a wound on an eye. The method includes gripping a portion of a conjunctiva adjacent to the wound using a pair of gripping surfaces at a distal end of a forceps, concurrently pressing a transparent projection against the wound while holding the portion of the conjunctiva, wherein the transparent projection is coupled to a lateral surface of the distal end of the forceps, and inserting one or more sutures to close the wound wherein the forceps stabilize the eye and the transparent projection presses fluids out of the way to enhance visibility of the wound.

Example 16 includes the method of example 15, further including removing a trocar cannula from the wound prior to gripping.

Example 17 includes the method of any one of examples 15-16, further including selecting from a first transparent projection on a first side of the forceps and a second transparent projection on a second side of the forceps.

Example 18 includes the method of any one of examples 15-17, wherein concurrently pressing the transparent projection against the wound while holding the portion of the conjunctiva includes concurrently pressing a substantially flat portion of a transparent projection against the wound.

These and other examples and features of the present infusion devices, and related methods will be set forth in part in the above detailed description. This overview is intended to provide non-limiting examples of the present subject matter—it is not intended to provide an exclusive or exhaustive explanation.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A forceps, comprising:
    a first arm, having a first gripping surface located at a distal end of the first arm;
    a second arm extending parallel to the first arm, having a second gripping surface located at a distal end of the second arm;
    a gripping region between the first and second gripping surfaces;
    a first lateral region on the first arm on a side opposite the gripping region;
    a bottom plane of the forceps defined by bottom edges of the first and second gripping surfaces; and
    a transparent projection extending from the first lateral region of the first arm, wherein a bottom surface of the transparent projection is within the bottom plane of the forceps.

2. The forceps of claim 1, wherein the first arm is connected to the second arm at a proximal end of the first and second arms.

3. The forceps of claim 1, wherein the transparent projection is formed from a polymeric material.

4. The forceps of claim 1, wherein the first and second arms are formed from stainless steel.

5. The forceps of claim 1, wherein the first and second arms are formed from a polymeric material, and the transparent projection is formed from a polymeric material.

6. The forceps of claim 5, wherein the first and second arms are co-molded with the transparent projection.

7. The forceps of claim 1, wherein the distal portion of the first and second arms is angled with respect to a proximal portion of the first and second arms.

8. The forceps of claim 1, wherein the transparent projection includes a cutout to allow closer insertion of a suture needle to a wound.

9. A forceps, comprising:
    a first arm, having a first gripping surface located at a distal end of the first arm;
    a second arm extending parallel to the first arm, having a second gripping surface located at a distal end of the second arm;
    a gripping region between the first and second gripping surfaces;
    a first lateral region on the first arm on a side opposite the gripping region;
    a second lateral region on the second arm on a side opposite the gripping region;
    a bottom plane of the forceps defined by bottom edges of the first and second gripping surfaces;
    a first transparent projection extending from the first lateral region of the first arm, wherein a bottom surface of the first transparent projection is within the bottom plane of the forceps; and
    a second transparent projection extending from the second lateral region of the second arm, wherein a bottom surface of the second transparent projection is within the bottom plane of the forceps.

10. The forceps of claim 9, wherein the distal portion of the first and second arms is angled with respect to a proximal portion of the first and second arms.

11. The forceps of claim 9, wherein the first and second transparent projections are formed from a polymeric material.

12. The forceps of claim 9, wherein the first and second arms are formed from stainless steel.

13. The forceps of claim 9, wherein the first and second arms are formed from a polymeric material, and the first and second transparent projections are formed from a polymeric material.

14. The forceps of claim 13, wherein the first and second arms are co-molded with the first and second transparent projections.

15. A method of suturing a wound on an eye, comprising:
    gripping a portion of a conjunctiva adjacent to the wound using a pair of gripping surfaces at a distal end of a forceps;
    concurrently pressing a transparent projection against the wound while holding the portion of the conjunctiva, wherein the transparent projection is coupled to a lateral surface of the distal end of the forceps; and
    inserting one or more sutures to close the wound wherein the forceps stabilize the eye and the transparent projection presses fluids out of the way to enhance visibility of the wound.

16. The method of claim 15, further including removing a trocar cannula from the wound prior to gripping.

17. The method of claim 15, further including selecting from a first transparent projection on a first side of the forceps and a second transparent projection on a second side of the forceps.

18. The method of claim 15, wherein concurrently pressing the transparent projection against the wound while holding the portion of the conjunctiva includes concurrently pressing a substantially flat portion of a transparent projection against the wound.

* * * * *